(12) United States Patent
Tamamushi

(10) Patent No.: US 8,229,207 B2
(45) Date of Patent: Jul. 24, 2012

(54) MASK INSPECTION APPARATUS AND MASK INSPECTION METHOD

(75) Inventor: Shuichi Tamamushi, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 484 days.

(21) Appl. No.: 12/560,962

(22) Filed: Sep. 16, 2009

(65) Prior Publication Data
US 2010/0074513 A1    Mar. 25, 2010

(30) Foreign Application Priority Data
Sep. 19, 2008    (JP) ................................ 2008-240619

(51) Int. Cl.
*G06K 9/00*    (2006.01)
(52) U.S. Cl. ...................................................... 382/144
(58) Field of Classification Search .................... 382/144
See application file for complete search history.

(56) References Cited

U.S. PATENT DOCUMENTS
7,655,904 B2 *   2/2010   Yamashita ..................... 250/306

FOREIGN PATENT DOCUMENTS
JP     2006-266864     10/2006

* cited by examiner

Primary Examiner — Roy M Punnoose
(74) Attorney, Agent, or Firm — Oblon, Spivak, McClelland, Maier & Neustadt, L.L.P.

(57) ABSTRACT

The present invention provides a mask inspection apparatus and method capable of eliminating distortion of each optical image, which is caused by distortions of mirrors and flexure of a mask, and performing a mask inspection with satisfactory accuracy. A stage with the mask held thereon is moved in X and Y directions and an optical image of each pattern written onto the mask is acquired while using the results of measurement by laser interferometers (Step S100). A positional displacement of the acquired optical image is corrected using polynomial equations in which pre-measured amounts of positional displacement of optical images have been fitted (Step S102). Each positional displacement that remains after the polynomial correction is corrected using a map descriptive of pre-measured amounts of positional displacements (S104). Each optical image subsequent to the map correction and a reference image are compared (Step S108).

9 Claims, 6 Drawing Sheets

MASK INSPECTION APPARATUS AND MASK INSPECTION METHOD

BACKGROUND OF THE INVENTION

1. Field of the Invention

The present invention relates to a mask inspection apparatus and method.

2. Background Art

To form each pattern on a substrate, a reticle or photomask (hereinafter referred to as "mask") is used in a manufacturing process of semiconductor devices. If the mask has a defect thereon, the defect is transferred onto the substrate. For that reason, a mask defect inspection needs to be carried out.

Examples of known mask inspection methods include a Die-to-Die inspection and a Die-to-Database inspection.

In the Die-to-Die inspection, optical images of the same pattern written at different positions of a mask are compared with each other. By contrast, in the Die-to-Database inspection, a reference image generated from design data (CAD data) used upon mask creation is compared with each of optical images of patterns written onto a mask.

In a mask inspection apparatus described in, for example, Japanese Patent Laid-open No. 2006-266864, the positions of a stage moved in X and Y directions in a state of a mask being held thereon are measured by laser interferometers. Each optical image is acquired using the results of measurement for comparison with a predetermined reference image.

As shown in FIG. 8 here, laser interferometers 112 and 114 respectively apply laser light to mirrors 111 and 113 provided at a stage 102 and receive light reflected by the mirrors 111 and 113 to thereby measure X-direction and Y-direction positions of the stage 102.

However, machining accuracy in polishing of each of these mirrors 111 and 113 is finite. Since the surfaces of the mirrors 111 and 113 are actually bent as shown in FIG. 8, positional displacements occur. Since a mask 101 supported by a support part 102a of the XY stage 102 is flexed by the influence of its gravity, for example, a positional displacement of Δx occurs in the X direction. When these positional displacements are combined together, an acquired optical image is distorted on the order of 20 nm to 30 nm as shown in FIG. 8. It was found that the distortion of the optical image is reproducible.

Since the reference image compared with each optical image is generated from the design data in the Die-to-Database inspection, such distortion as mentioned above does not occur. It was therefore difficult to perform a mask inspection with satisfactory accuracy.

Recently, miniaturization and higher densification of circuit patterns for a semiconductor device have been advanced and its resolution is approaching its limit. Therefore, a double patterning or double exposure technology for dividing a pattern into two masks and transferring high-density patterns using these two masks has been studied.

The registration or alignment of patterns for the two masks employed in the double patterning is required with a high accuracy of about 2 nm to 3 nm. Thus, when the masks used in the double patterning are inspected in particular, optical images obtained from the masks need not to have local distortion. However, the optical images are actually distorted on the order of 20 nm to 30 nm. It was thus difficult to satisfy this need.

The present invention has been made in view of the foregoing problems. That is, an object of the present invention is to provide a mask inspection apparatus and method capable of eliminating distortion of each optical image, which is caused by distortions of mirrors and flexure of a mask, and performing a mask inspection with satisfactory accuracy.

SUMMARY OF THE INVENTION

According to one aspect of the present invention, a mask inspection apparatus comprises a stage having a first mirror and a second mirror and movable in X and Y directions in a state of holding a mask thereon, a first laser interferometer for applying laser light to the first mirror and receiving light reflected therefrom to thereby measure an X-direction position of the stage, a second laser interferometer for applying laser light to the second mirror and receiving light reflected therefrom to thereby measure a Y-direction position of the stage, an optical image acquisition part for moving the stage in the X and Y directions and acquiring optical images of patterns written onto the mask while using the results of measurement by the first and second laser interferometers, a positional displacement amount storage part for storing therein pre-measured amounts of positional displacements of optical images, which are caused by flexure of the mask and distortions of the first and second mirrors, a positional displacement correction part for correcting positional displacements of the optical images acquired by the optical image acquisition part, based on the positional displacement amounts stored in the positional displacement amount storage part, and an image comparison part for comparing each of the optical images corrected by the positional displacement correction part and a predetermined reference image.

According to another aspect of the present invention, in a mask inspection method, a stage with a mask held thereon is moved in X and Y directions, is measured X-direction and Y-direction positions of the stage by laser interferometers, and is acquired an optical image of each pattern written onto the mask while using the results of measurement thereby. A pre-stored amount of positional displacement of each optical image, which is caused by flexure of the mask and distortions of mirrors reflecting laser light applied from the laser interferometers is read, and is corrected the acquired positional displacement of the optical image based on the read amount of positional displacement. Each corrected optical image and a predetermined reference image is compared.

Another object and advantages of the present invention will become apparent from the following description.

DETAILED DESCRIPTION OF THE EMBODIMENTS

Figure 1:
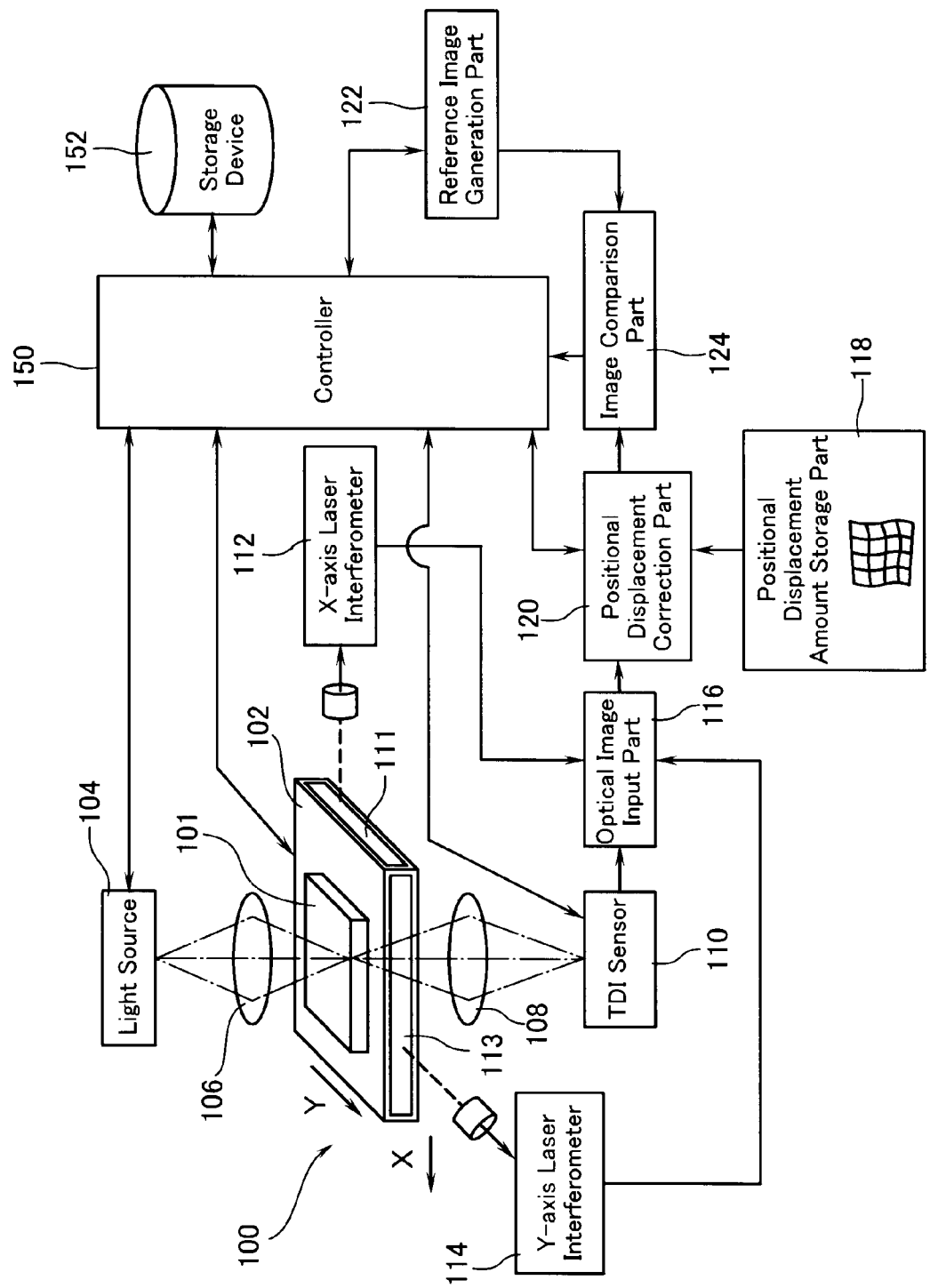
FIG. 1 is a conceptual diagram showing a configuration of a mask inspection apparatus 100 according to an embodiment of the present invention.

FIG. 1 is a conceptual diagram showing a configuration of a mask inspection apparatus 100 according to an embodiment of the present invention. The mask inspection apparatus 100 is equipped with a stage 102 for holding a mask 101 to be inspected thereon. The stage 102 holds the mask 101 by a holding part 102a shown in FIG. 8.

The stage 102 is drivable in X and Y directions by a motor not shown in the figure. Driving control of the stage 102 is executed by a controller 150. The controller 150 executes the entire control related to a mask inspection.

A mirror 111 is provided at a side surface of the stage 102, which is parallel to the Y direction. An X-axis laser interferometer 112 is disposed opposite to the mirror 111. The X-axis laser interferometer 112 emits laser light to the mirror 111 and receives light reflected by the mirror 111 to thereby measure an X-direction position of the stage 102.

Similarly, a mirror 113 is provided at a side surface of the stage 102, which is parallel to the X direction. A Y-axis laser interferometer 114 is disposed opposite to the mirror 113. The Y-axis laser interferometer 114 emits laser light to the mirror 113 and receives light reflected by the mirror 113 to thereby measure a Y-direction position of the stage 102.

Results of measurements by the X-axis and Y-axis laser interferometers 112 and 114 are transmitted to an optical image input part 116, which in turn are used for generation of each optical image.

The mask inspection apparatus 100 is equipped with a light source 104 that emits laser light. The laser light emitted from the light source 104 is applied to the mask 101 via a contact lens 106 that configures a transmitted illumination optical system.

The laser light transmitted through the mask 101 is image-formed onto a TDI sensor corresponding to a transmitted light detection part 110 via an objective lens 108. The TDI sensor 110 has an imaging area shaped in the form of a rectangle (2048 pixels×512 pixels, for example). Incidentally, the size of one pixel ranges from 70 nm×70 nm, for example.

Although not shown in the figure, the TDI sensor 110 comprises a plurality of stages (512 stages, for example) of lines arranged in a TDI direction (charge storage direction). The respective lines respectively comprise a plurality of pixels (2048 pixels, for example) arranged in the direction orthogonal to the TDI direction.

The TDI sensor 110 is disposed in such a manner that the TDI direction and the X direction of the stage 102 coincide with each other. Thus, when the stage 102 is moved in the X direction, the TDI sensor 110 is moved relative to the mask 101, so that a pattern of the mask 101 is imaged or captured by the TDI sensor 110 (refer to FIG. 2).

Incidentally, the TDI sensor 110 is configured so as to be capable of outputting electrical charges from a dual direction.

An output (optical image) corresponding to one line of the TDI sensor 110 is amplified by an unillustrated amplifier, followed by being stored into the optical image input part 116. At this time, the optical image corresponding to one line is stored in association with the X-direction and Y-direction positions measured by the X-axis and Y-axis laser interferometers 112 and 114.

Figure 2:
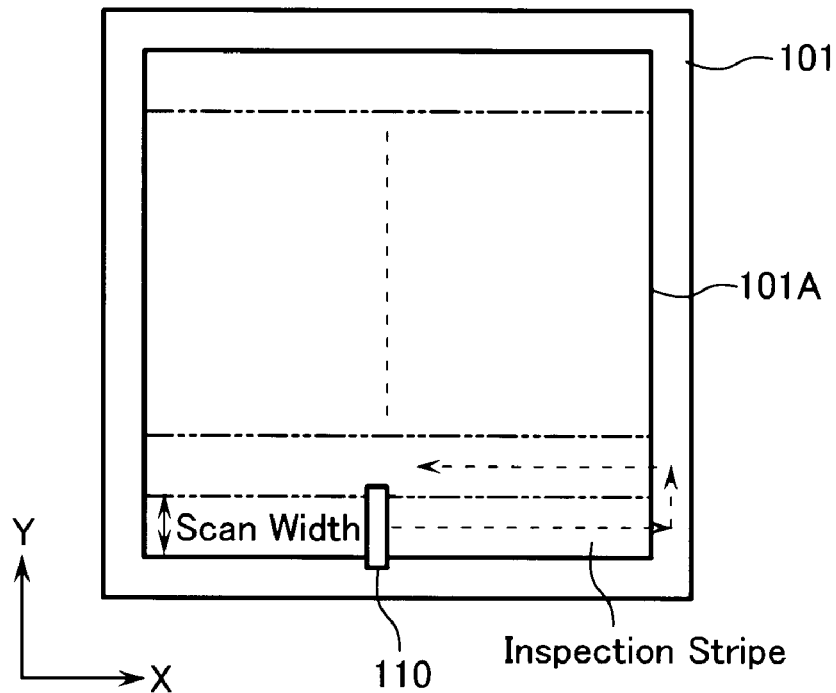
FIG. 2 is a conceptual diagram showing inspection stripes of a mask 101.

As shown in FIG. 2, an inspected area or region 101A of the mask 101 is virtually divided into a plurality of inspection stripes of strip form along the Y direction. The width (scan width) of each inspection stripe is set according to the length of each line of the TDI sensor 110.

While the stage 102 is continuously moved in the X direction in a state in which the mask 101 is being held, an optical image at one of the virtually-divided inspection stripes is imaged or captured by the TDI sensor 110. When the end of the inspection stripe is reached, the stage 102 is moved in the Y direction. Thereafter, an optical image at the next inspection stripe is imaged by the TDI sensor 110 while the stage 102 is continuously moved in the opposite X direction. By repeating this operation, optical images in the entire inspected area of the mask 101 are acquired by the optical image input part 116.

Figure 8:
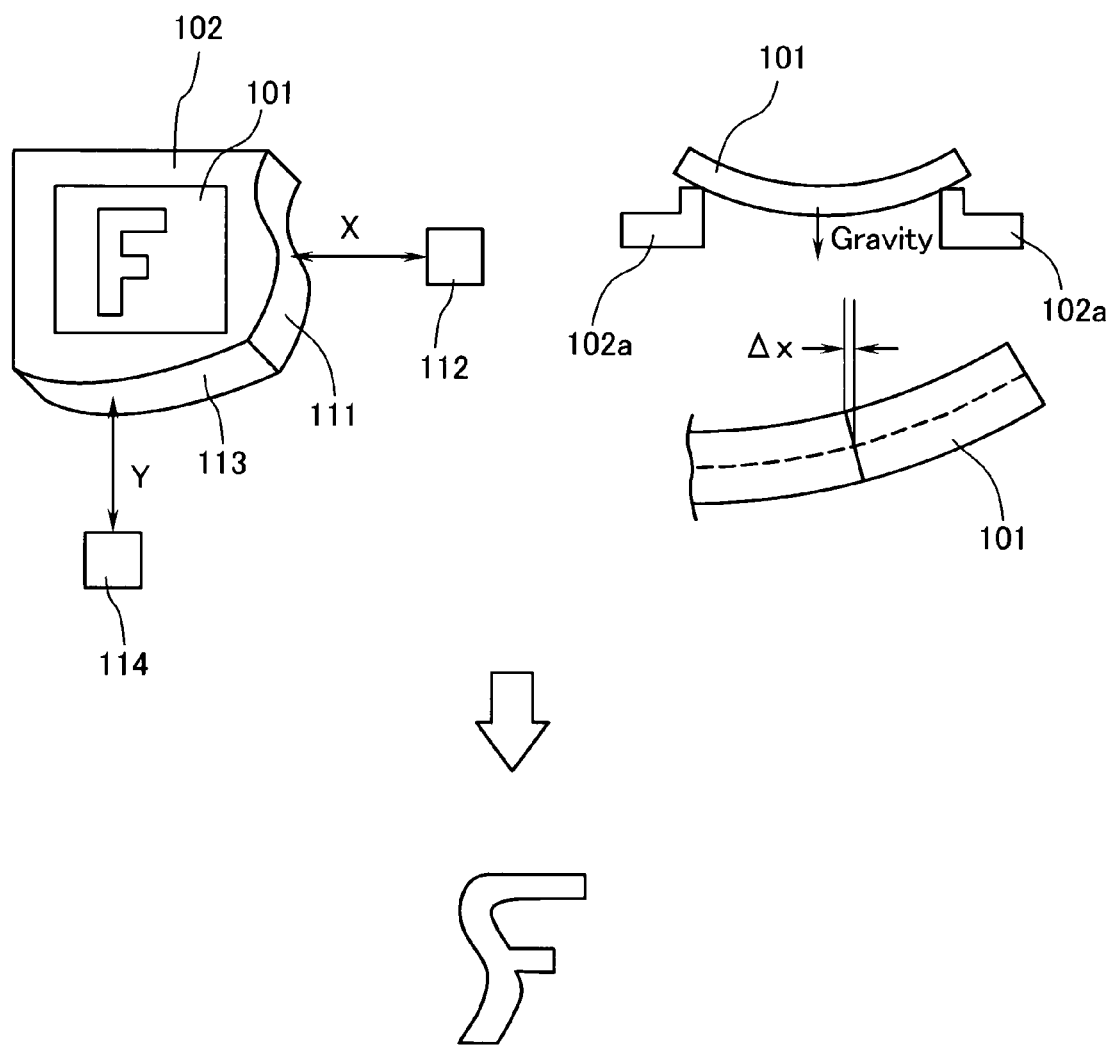
FIG. 8 is a conceptual diagram explaining of distortion of a optical image causing by distortions of mirrors and flexure of a mask flexing by the influence of its gravity.

The optical images acquired by the optical image input part 116 are affected by positional displacements caused by the distortions of the mirrors 111 and 113 and flexure of the mask 101 due to the gravity thereof as mentioned above. Such distortion as shown in FIG. 8 occurs.

Thus, in the present embodiment, the amounts of positional displacements caused by the distortions of the mirrors 111 and 113 and the flexure of the mask 101 are measured in advance by a method to be described later. The measured amounts of positional displacements are stored in a positional displacement amount storage part 118.

Figure 3:
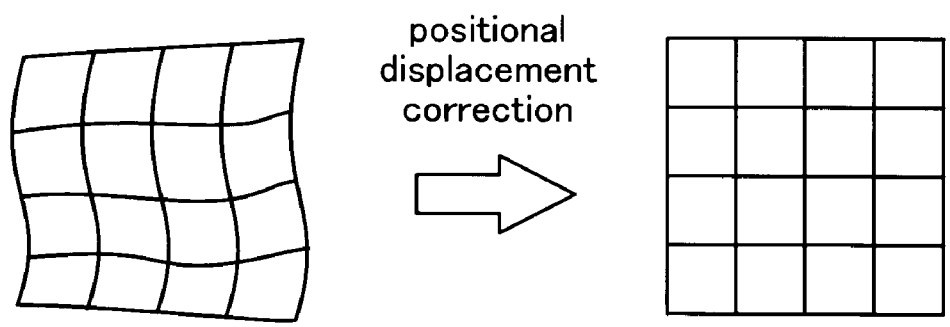
FIG. 3 is a conceptual diagram showing positional displacement correction of coordinates.

A positional displacement correction part 120 corrects (reverse-corrects) the positional displacement of each optical image inputted from the optical image input part 116 using the amounts of positional displacements stored in the positional displacement amount storage part 118 as shown in FIG. 3. That is, the positional displacement correction part 120 executes Grid Matching Correction (GMC) for each optical image.

The measurement and storage of each positional displacement amount, which are performed before the inspection of the mask, will next be explained with reference to FIGS. 4 through 6.

Figure 4:
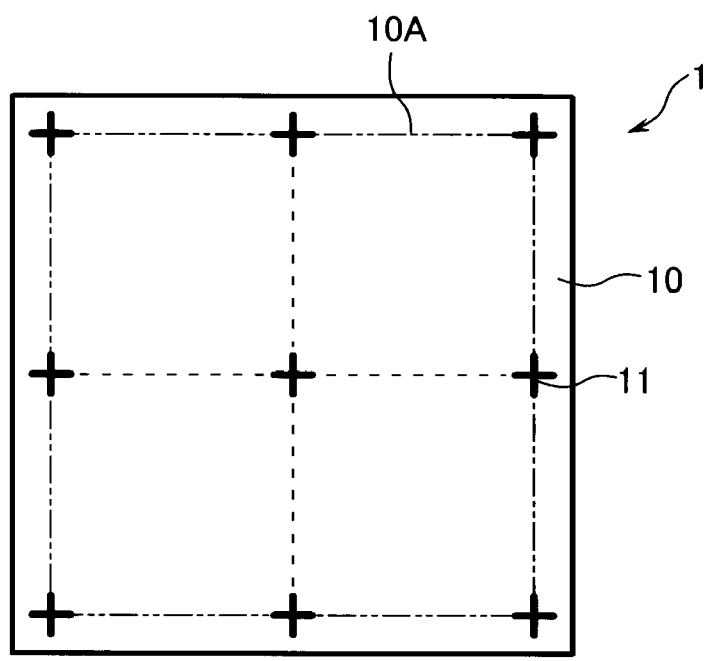
FIG. 4 is a schematic diagram showing a mask 1 used in the measurement of each positional displacement amount.

FIG. 4 is a schematic diagram showing a mask 1 used in the measurement of each positional displacement amount. The mask 1 is one in which a plurality of cross marks 11 each composed of a chromium film are regularly formed in an area 10A of a transparent substrate (glass substrate, for example) 10. The centers (intersections) of the marks 11 are disposed by an ideal system of coordinates at equal intervals. Incidentally, the area 10A corresponds to the inspected area 101A.

The mask 1 is placed on the stage 102 to acquire optical images of the marks 11 while the stage 102 is driven in the X and Y directions. The positions of the marks 11 are determined from the acquired optical images.

Figure 5:
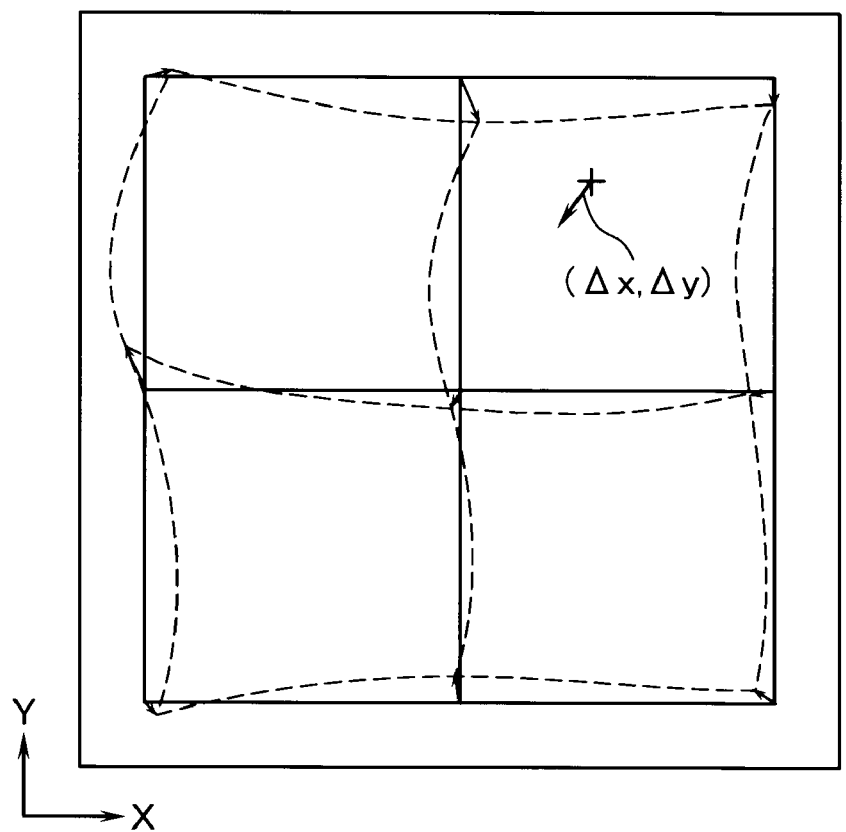
FIG. 5 is one map indicative of the amounts of positional displacements of respective marks.

FIG. 5 is one map indicative of the amounts of positional displacements of respective marks. In the example shown in FIG. 5, the positions of marks at nine points (3×3 points) in an ideal coordinate system indicated by a solid line are displaced as indicated by broken lines. That is, the positions of the marks at the nine points are respectively displaced by quantities (vector quantities) indicated by arrows in the figure.

Using the amounts of positional displacements at the nine points, the amounts of positional displacements ($\Delta x$, $\Delta y$) at arbitrary coordinates (x, y) on the stage 102 are fitted into 3rd order polynomial equations expressed in the following equations (1) and (2). That is, parameters $a_0$ through $a_9$ of the 3rd order polynomial equation (1) in the X direction, and parameters $b_0$ through $b_9$ of the 3rd order polynomial equation (2) in the Y direction are determined by fitting:

$$\Delta x = a_0 + a_1 x + a_2 y + a_3 x^2 + a_4 xy + a_5 y^2 + a_6 x^3 + a_7 x^2 y + a_8 xy^2 + a_9 y^3 \quad (1)$$

$$\Delta y = b_0 + b_1 x + b_2 y + b_3 x^2 + b_4 xy + b_5 y^2 + b_6 x^3 + b_7 x^2 y + b_8 xy^2 + b_9 y^3 \quad (2)$$

The determined parameters $a_0$ through $a_9$ and parameters $b_0$ through $b_9$ are stored in the positional displacement amount storage part 118 and used upon correction of the positional displacement of each optical image by the positional displacement correction part 120.

Incidentally, the polynomial equations used for fitting are not limited to the 3rd order polynomial equations such as expressed in the above equations (1) and (2), but may be polynomial equations of four or more orders.

The positional displacement correction (hereinafter referred to as "polynomial correction") using the parameters is effective where each positional displacement is smooth. Specifically, if the difference between a displacement amount for a coordinate and a displacement amount for a coordinate around the former coordinate falls within a predetermined range, then polynomial correction is effective. In contrast, if a displacement amount for a particular coordinate is prominent in comparison with those for other coordinates, i.e., if the difference between a displacement amount for a coordinate and a displacement amount for a coordinate around the former coordinate exceeds a predetermined range, then the positional displacement correction using the parameters may not cope with it. In this case, correction based on a map is effective.

Figure 6:
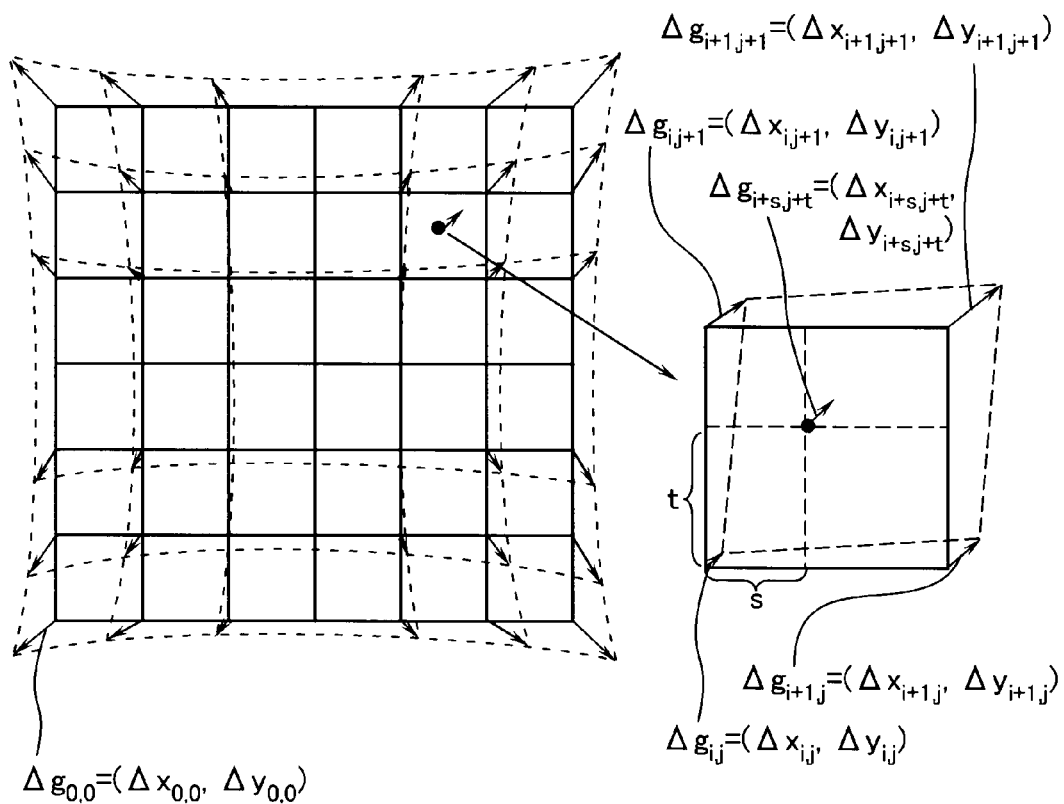
FIG. 6 is another map indicative of the amounts of positional displacements of respective marks.

FIG. 6 is another map indicative of the amounts of positional displacements of respective marks. In the example shown in FIG. 6, the positions of marks at forty-nine points (7×7 points) in an ideal coordinate system indicated by a solid line are displaced as indicated by broken lines. The map shown in FIG. 6 is stored in the positional displacement amount storage part 118 and used upon correction of the positional displacement of each optical image by the positional displacement correction part 120.

The amounts of positional displacements $\Delta g$ ($\Delta x_{x,y}$, $\Delta y_{x,y}$) at arbitrary coordinates g (x, y) in the ideal coordinate system indicated by the solid line in FIG. 6 may be determined by an interpolation method from the amounts of positional displacements at four points at the periphery that surrounds the coordinates g (x, y).

For example, the amounts of positional displacements $\Delta g_{i+s,j+t}$ ($\Delta x_{i+s,j+t}$, $\Delta y_{i+s,j+t}$) at coordinates g (i+s, j+t) in FIG. 6 can be determined by the following equations (3) and (4):

$$\Delta x_{i+s,j+t} = \Delta x_{i,j}(1-s)(1-t) + \Delta x_{i+1,j}s(1-t) + \Delta x_{i,j+1}(1-s)t + \Delta x_{i+1,j+1}st \quad (3)$$

$$\Delta y_{i+s,j+t} = \Delta y_{i,j}(1-s)(1-t) + \Delta y_{i+1,j}s(1-t) + \Delta y_{i,j+1}(1-s)t + \Delta y_{i+1,j+1}st \quad (4)$$

The mask inspection apparatus 100 shown in FIG. 1 is equipped with a reference image generation part 122. The reference image generation part 122 generates a reference image from design data (CAD data) at generation of a mask stored in a storage device 152.

The reference image generated by the reference image generation part 122 is inputted to an image comparison part 124. The image comparison part 124 compares the reference image and each optical image whose positional displacement has been corrected by the positional displacement correction part 120 and outputs the result of comparison (result of inspection) to the controller 150.

A mask inspection method according to the present embodiment will next be explained with reference to FIG. 7. A routine shown in FIG. 7 is executed by the controller 150.

Figure 7:
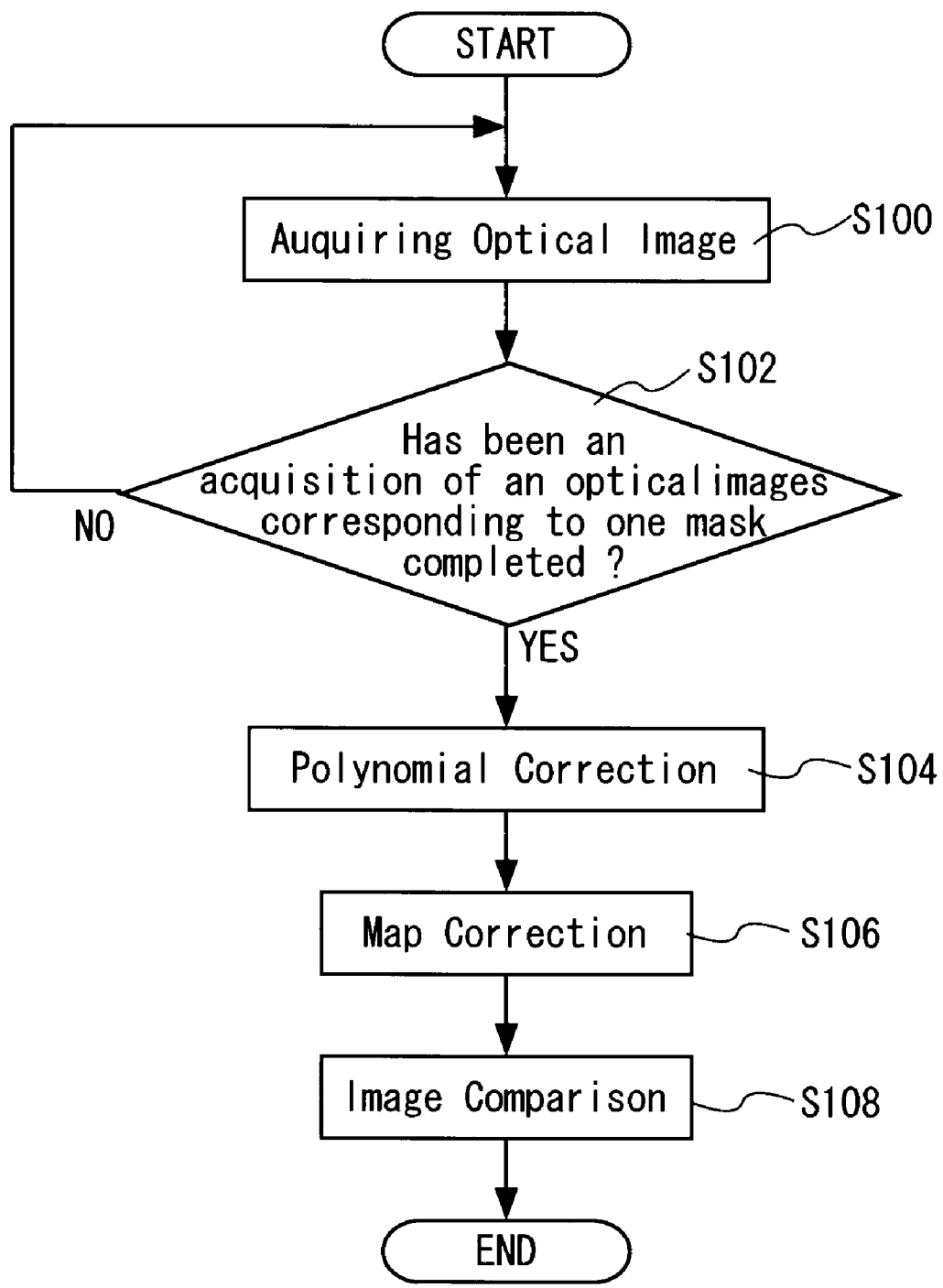
FIG. 7 is a flowchart explaining of a mask inspection method according to the present embodiment.

According to the routine shown in FIG. 7, each optical image is first acquired (Step S100). At Step S100, the optical images imaged or captured by the TDI sensor 110 while the XY stage is being moved in the X and Y directions, are sequentially stored in the optical image input part 116. At this time, the optical images are combined using the results of measurement by the laser interferometers 112 and 114.

It is next determined whether the acquisition of the optical images corresponding to one mask has been completed (Step S102). It is determined at Step S102 whether all of the optical images of the inspected area 101A in the mask 101 have been acquired. When it is determined at Step S102 that the acquisition of the optical images corresponding to one mask has not yet been completed, the routine returns to the process of Step S100 referred to above.

On the other hand, when it is determined at Step S102 that the acquisition of the optical images corresponding to one mask has been ended, the positional displacements of the optical images acquired at Step S100 are corrected by the positional displacement correction part 120 using the parameters $a_0$ through $a_9$ and $b_0$ through $b_9$ (Step S104). At Step S104, the parameters $a_0$ through $a_9$ and $b_0$ through $b_9$ of the above equations (1) and (2) stored in the positional displacement amount storage part 118 are read. The positional displacements of the optical images in the X and Y directions are corrected according to the 3rd order polynomial equations (1) and (2) with these parameters inputted therein.

Thereafter, the positional displacement correction part 120 corrects the positional displacements that still remain in part of the optical images even depending on the polynomial correction of above Step S104, using the map (Step S106). At Step S106, such a map as shown in FIG. 6 stored in the positional displacement amount storage part 118 is read and the positional displacements at the part of the optical images are corrected using the map.

Incidentally, the part that needs map correction, i.e., part large to such an extent that the positional displacement of each optical image is not smooth in comparison with a peripheral part and cannot be corrected in the case of the polynomial correction can be specified upon creation of the map. Therefore, the map correction may be performed on the specified part at Step S106 referred to above.

Finally, each optical image subsequent to the map correction and the reference image generated by the reference image generation part 122 are compared by the image comparison part 124 (Step S108). The result of comparison (result of inspection) is sent to the controller 150 and displayed on an unillustrated display part.

In the present embodiment as described above, the amounts of positional displacements of the optical images, which are caused by the distortions of the mirrors 111 and 113 and flexure of the mask 101 due to the gravity thereof are measured in advance. The measured positional displacement amounts are stored in the positional displacement amount storing part 118 as the polynomial equations and map. The positional displacements of the optical images are corrected by the positional displacement correction part 120 using the polynomial equations and map. Thus, distortion of each optical image caused by the distortions of the mirrors 111 and 113 and the flexure of the mask 101 due to the gravity thereof can be eliminated, thereby making it possible to perform a mask inspection with satisfactory accuracy. Accordingly, the present invention is suitable for application to the inspection of the mask employed in double patterning.

Such positional displacements that their correction cannot be performed by the polynomial correction can be corrected by performing the map correction after the execution of the polynomial correction.

Incidentally, the present invention is not limited to the above embodiment, but can be modified in various ways within the scope not departing from the gist of the present invention. Although the optical images have been acquired using the transmitted illumination system in the present embodiment, for example, the present invention is not limited to it. The present invention is applicable even to the case where optical images are acquired using a reflected illumination system.

Although the above embodiment has explained the example of the die-to-database inspection which compares each optical image subsequent to the positional displacement correction and the reference image generated from the design data, the present invention can be applied to a die-to-die inspection which compares optical images with each other. In this case, the optical images subsequent to the positional displacement correction may be compared with each other.

Although both of the polynomial correction and the map correction have been carried out in the above embodiment, either one of the two may be executed according to the degree of distortion of each optical image.

The features and advantages of the present invention may be summarized as follows.

In the first aspect of the present invention, the amounts of positional displacements of optical images, which are caused by flexure of a mask and distortions of first and second mirrors, are measured in advance. The measured positional displacement amounts are stored in a positional displacement amount storage part. The positional displacements of the optical images acquired by the optical image acquisition part are corrected by the positional displacement correction part, based on the stored positional displacement amounts. According to the first aspect, distortion of each optical image, which is caused by the distortion of each mirror and flexure of the mask can be eliminated and the inspection of the mask can be carried out with satisfactory accuracy.

In the second aspect of the present invention, an optical image of each mask pattern is acquired. Afterwards, the pre-stored amount of positional displacement of each optical image, which is caused by the flexure of the mask and the distortion of each mirror, is read. A positional displacement of the acquired optical image is corrected based on the read amount of positional displacement. According to the second aspect, distortion of each optical image, which is caused by the distortion of each mirror and the flexure of the mask, can be eliminated, and the inspection of the mask can be performed with satisfactory accuracy.

Obviously many modifications and variations of the present invention are possible in the light of the above teachings. It is therefore to be understood that within the scope of the appended claims the invention may be practiced otherwise than as specifically described.

The entire disclosure of a Japanese Patent Application No. 2008-240619, filed on Sep. 19, 2008 including specification, claims, drawings and summary, on which the Convention priority of the present application is based, are incorporated herein by reference in its entirety.

What is claimed is:

1. A mask inspection apparatus comprising:
a stage having a first mirror and a second mirror and movable in X and Y directions in a state of holding a mask thereon;
a first laser interferometer for applying laser light to the first mirror and receiving light reflected therefrom to thereby measure an X-direction position of the stage;
a second laser interferometer for applying laser light to the second mirror and receiving light reflected therefrom to thereby measure a Y-direction position of the stage;
an optical image acquisition part for moving the stage in the X and Y directions and acquiring optical images of patterns written onto the mask while using the results of measurement by the first and second laser interferometers;
a positional displacement amount storage part for storing therein pre-measured amounts of positional displacements of optical images, which are caused by flexure of the mask and distortions of the first and second mirrors;
a positional displacement correction part for correcting positional displacements of the optical images acquired by the optical image acquisition part, based on the positional displacement amounts stored in the positional displacement amount storage part; and
an image comparison part for comparing each of the optical images corrected by the positional displacement correction part and a predetermined reference image.

2. The mask inspection apparatus according to claim 1, wherein the optical image acquisition part acquires the images of patterns written onto the mask using a TDI sensor having a plurality of stages of lines.

3. The mask inspection apparatus according to claim 1, wherein the positional displacement amount storage part stores therein parameters determined by fitting pre-measured positional displacement amounts into polynomial equations and a map descriptive of pre-measured positional displacement amounts, and
wherein the positional displacement correction part corrects the positional displacement of each optical image acquired by the optical image acquisition part, using at least one of the parameters and the map.

4. The mask inspection apparatus according to claim 1, further comprising an image generation part and a storage device for storing design data at mask generation,
wherein the image generation part generates the predetermined reference image from the design data.

5. A mask inspection method comprising:
moving a stage with a mask held thereon in X and Y directions, measuring X-direction and Y-direction positions of the stage by laser interferometers and acquiring an optical image of each pattern written onto the mask while using the results of measurement thereby;
reading a pre-stored amount of positional displacement of each optical image, which is caused by flexure of the mask and distortions of mirrors reflecting laser light applied from the laser interferometers, and correcting the positional displacement of the acquired optical image based on the read amount of positional displacement; and
comparing each corrected optical image and a predetermined reference image.

6. The mask inspection method according to claim 5, further comprising:
reading parameters determined by fitting the positional displacement amounts measured in advance into polynomial equations; and
correcting the positional displacement of each acquired optical image using the parameters.

7. The mask inspection method according to claim 6, further comprising:
reading a map descriptive of the positional displacement amounts measured in advance; and
using the map to correct a positional displacement of each optical image remaining after the correction of the positional displacement of the optical image based on the parameters.

8. The mask inspection method according to claim 5, further comprising:
   reading a map descriptive of the positional displacement amounts measured in advance; and
   using the map to correct the positional displacement of the optical image.

9. The mask inspection method according to claim 5, wherein the predetermined reference image is generated from design data at mask generation.

* * * * *